United States Patent [19]
Dogan et al.

[11] Patent Number: 5,630,844
[45] Date of Patent: May 20, 1997

[54] BIOCOMPATIBLE HYDROPHOBIC LAMINATE WITH THERMOPLASTIC ELASTOMER LAYER

[75] Inventors: Aydin Dogan, Köln, Germany; Kenneth C. Kredovski; Adam D. Kredovski, both of Roseville, Minn.; Thomas G. Hayes, Minneapolis, Minn.

[73] Assignee: Novamed Medical Products Manufacturing, Inc., Minneapolis, Minn.

[21] Appl. No.: 473,284

[22] Filed: Jun. 7, 1995

[51] Int. Cl.⁶ ............................................. A61F 2/12
[52] U.S. Cl. ........................... 623/8; 623/11; 427/2.24
[58] Field of Search ..................... 623/8, 11; 428/35.7, 428/412, 425.5, 447; 427/2.24, 2.3, 333, 336, 387, 393.5

[56] References Cited

U.S. PATENT DOCUMENTS 4,413,359  11/1983  Akiyama et al. .
4,992,312  2/1991  Frisch ............................................. 623/8
5,302,393  4/1994  Matsumoto et al. ........................ 623/11

FOREIGN PATENT DOCUMENTS 0143994  6/1985  European Pat. Off. .
9000827  8/1990  WIPO .

*Primary Examiner*—John G. Weiss
*Assistant Examiner*—Francis K. Cuddihy

[57] ABSTRACT

A biocompatible hydrophobic laminate. The laminate structure includes one layer of a rubber, such as silicone rubber, which is biocompatible with the inside of the body. The laminate structure further includes a hydrophobic layer or membrane formed of a thermoplastic elastomer such as a styrene triblock copolymer. The triblock copolymer may contain styrene endblocks with an elastomeric midblock such as polyisoprene, polybutadiene, polyisobutylene, and poly(ethylene-co-butylene). The laminate structure may be utilized for structures to be introduced into the body, such as for a breast prosthesis shell or a coating for a catheter.

32 Claims, 3 Drawing Sheets

BIOCOMPATIBLE HYDROPHOBIC LAMINATE WITH THERMOPLASTIC ELASTOMER LAYER

BACKGROUND

The present invention relates to shells or envelopes or coatings for enveloping matter or an object that is to be introduced into the human body, and more particularly to laminate structures with hydrophobic thermoplastic elastomer membranes.

Breast implants, testes prosthesis, penile implants, catheters, and pacemakers are but a few examples of invasive structures. Many if not all of such invasive structures have moisture related problems. For example, the shell of a breast implant may permit moisture into the shell which may lead to a swelling of the implant. Conversely, moisture permeation out of the shell may bring about a phenomenon referred to as fold flaw fracture, where the sides of the shell may rub against each other and hence induce a tearing of the shell. Testes prostheses and penile implants likewise typically include a mass of filling material which may be affected by moisture permeation into or out of the prostheses or implant. Catheters and pacemakers typically include metal components which may be corroded by moisture in the body.

SUMMARY OF THE INVENTION

A general object of the invention is to provide a unique water impermeable laminate structure.

Another object of the invention is to provide such a water impermeable laminate structure for uniquely coating or enveloping an invasive structure to be introduced into the human body or a structure which comes into contact with the inside of the body, or body tissue or fluid.

Another object of the invention is to provide such a laminate structure which uniquely includes a thermoplastic elastomer. A conventional elastomer is a natural or synthetic polymer which at room temperature can be stretched repeatedly to at least twice its original length and which after removal of the tensile load will immediately and forcibly return to, approximately, its original length. The glass transition temperature of a typical elastomer is well below room temperature such that the elastomer is soft, flexible, and resilient at room temperature. The processing of elastomers is relatively slow, is irreversible, and requires heat to change from a processible melt to a rubber like object. A thermoplastic is a plastic material with a glass-rubber transition temperature well above room temperature such that the thermoplastic is relatively hard at room temperature. A thermoplastic material softens on heating and hardens on cooling, with the heating/cooling cycle being rapid and repeatable. Unlike elastomers, a thermoplastic changes from a processible melt to a solid object upon cooling. A thermoplastic elastomer displays the typical high elasticity of an elastomer, but may be processed as a thermoplastic. Thermoplastic elastomers, instead of being cross-linked through covalent bonds by vulcanization like conventional elastomers, have their polymer chains tied together by physical crosslinks. These physical crosslinks are broken by heating and reformed upon cooling. With a thermoplastic elastomer, the manufacturing of a moisture vapor barrier for an invasive structure such as a breast implant shell is more manageable and leads to a safer breast implant.

Another object of the present invention is to provide a thermoplastic elastomer moisture vapor barrier laminate structure that uniquely includes block copolymers. Block copolymers are polymers in which chemically different blocks or sequences bind to each other in macromolecular chains. The effects of the blocks are asserted individually in the block copolymer. The four main classes of block copolymers are diblocks, triblocks, multiblock and star (or radial) block copolymers. For example, a triblock thermoplastic copolymer may be designated as ABA with "A" representing a thermoplastic polymer block and "B" representing a elastomer polymer block. Such a triblock copolymer may thus have both thermoplastic and elastomeric properties. A safer invasive structure is the result.

Another object of the invention is to provide a thermoplastic elastomer moisture vapor barrier which uniquely includes a block copolymer having styrene endblocks. It has been found that such styrene block copolymers form strong and compatible laminate structures with silicone rubber and polyurethane envelopes. Thus a safer invasive structure is provided.

Another object of the invention is to provide a thermoplastic elastomer moisture vapor barrier which uniquely includes an elastomer midblock selected from olefinic, vinyl, and dienyl based polymers. It has been found that such elastomer midblocks form strong, hydrophobic and compatible laminate structures with silicone rubber and polyurethane envelopes. A safer invasive structure is thereby provided.

Another object of the invention is to provide a thermoplastic elastomer fluid barrier with a unique mixture of thermoplastic elastomers. An even safer invasive structure such as a breast implant may therefore be provided.

Another object of the invention is to provide a breast prosthesis shell that uniquely includes a hydrophobic thermoplastic elastomer layer. A breast implant is an elastomeric envelope having a filling material therein, and closure means to seal the filling material in the envelope. The elastomeric envelope may be formed of silicone rubber or polyurethane. The filling material may be oil-based, such as with a silicone gel or a vegetable oil, or water based, such as normal saline, or a water soluble base of carboxymethyl cellulose, polyvinylpyrrolidinone, or polyethylene oxide. The closure means may include valves including compression valves, leaf valves, septa, and room temperature vulcanized silicone button seals. The silicone rubber or polyurethane envelope or shell is permeable to water vapor. This allows facile transfer of water into and out of the envelope when an osmotic imbalance between the filling material and the body exists. For this reason, water based filling material are conventionally limited to those materials which can be formulated to approximate an osmotic balance similar to physiological fluids (ca. 311 mOsmole/kg). In many instances, these limitations prohibit the use of viscous solutions that approximate the texture and feel of human tissue. When filled with physiological saline based filling material, silicone rubber implants have ruptured through fold flaw fracture caused by loss of water vapor and the attendant partial collapse of the implant. This mechanism is thought to arise from the mechanical scission of the bonds in the silicone polymer induced by local friction of the partially collapsed implant causing thermal degradation. The present unique thermoplastic water vapor barrier thereby provides a greater variety of filling materials for the breast implant, as well as providing for a safer breast implant by, for example, maintaining the biocompatible water based filling material at the desired osmotic balance in the shell.

Another object of the invention is to provide a catheter with a coating having a unique water vapor barrier. A catheter may include an inner axial extending metal lead or pair of leads inside of a metal coil which supplies structure to the catheter but permits a flexing thereof. Since these metal elements are subject to corrosion by moisture in the body, the metal used is often metal which is resistant to corrosion, such as gold or titanium. With the coating or laminate of the present invention, less expensive metal may be utilized and more economical catheters may be made available.

Another object of the invention is to provide a unique laminate structure having one rubber layer which is compatible with the inside of the body, and a hydrophobic thermoplastic elastomer membrane with an $H_2O$ permeability coefficient of 2,290 or less.

Another object of the invention is to provide a unique laminate structure having one rubber layer which is compatible with the inside of the body, and includes a hydrophobic thermoplastic elastomer impervious membrane, where the laminate structure further has a tensile strength of over 900 pounds per square inch (63.3 kilograms per square centimeter), is elongatable up to 1000% without delamination, and has a tear resistance of over 100 pounds per inch (17.9 kilograms per centimeter).

Another object of the invention is to provide such a laminate structure which is uniquely relatively inexpensive. Thermoplastic elastomers, besides being more manageable than materials such as thermosets, are generally less expensive.

Surprisingly, all of the above objectives can be satisfied by the preferred teachings of the present invention, detailed descriptions of which are provided below.

Figure 1:
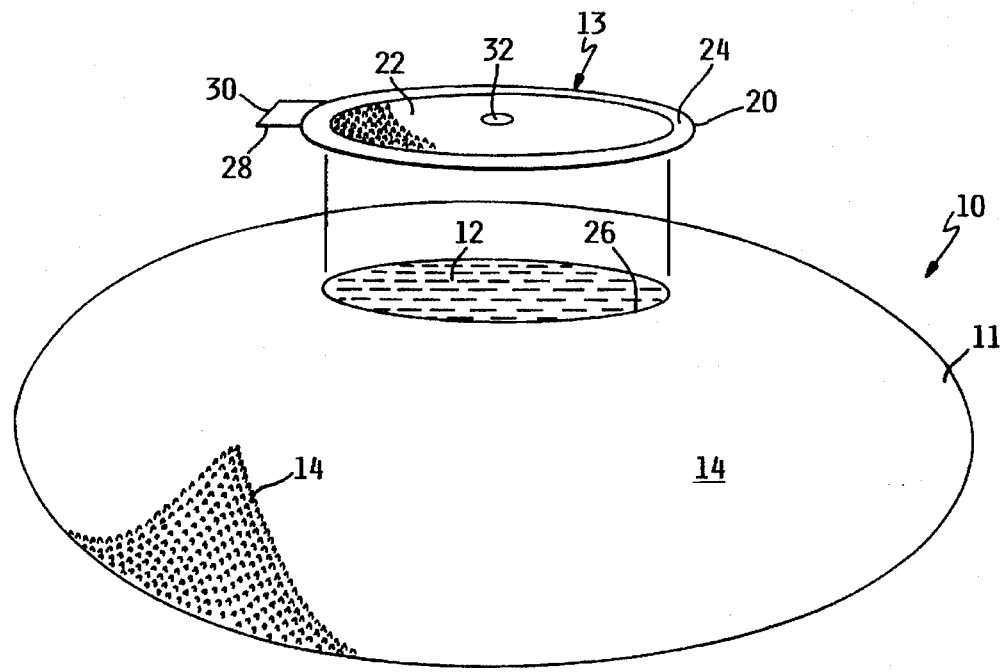
FIG. 1 shows a perspective view of a preferred form of the breast implant according to the preferred teachings of the present invention.

All Figures are drawn for ease of explanation of the basic teachings of the present invention only; the extensions of the Figures with respect to number, position, relationship, and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in the various figures of the drawings, the same numerals designate the same or similar parts. Furthermore, when the terms "axial", "outer" and "inner" and similar terms are used herein, it should be understood that these terms have reference only to the structure shown in the drawings as it would appear to a person viewing the drawings and are utilized only to facilitate describing the preferred embodiment.

DETAILED DESCRIPTION OF THE PREFERRED EMBODIMENTS

As shown in FIG. 1, a breast implant is generally designated by reference numeral 10. The breast implant 10 includes a shell 11, a filling material 12, and a closure or joint 13 for closing the shell 11 and sealing the filling material therein. The shell 11 is preferably a laminate of three layers: an outer layer 14 of preferably silicone rubber, a middle layer 15 of preferably a thermoplastic elastomer such as styrene block copolymers, or a mixture of styrene block copolymers and ethylene-propylene based copolymers which are thermoplastic elastomers, and an inner layer 16 of preferably silicone rubber. The filling material 12 may be chosen from a wide variety of materials, including but not limited to oil-filled implants such as silicone or silicone gel or vegetable oil implants, and aqueous based solution implants such as normal saline, water soluble polymer based material such as polyvinylpyrrolidinone, polyethylene oxide, or polyols, and water dispersible systems including cellulosic based gels such as carboxymethyl cellulose.

Figure 2:
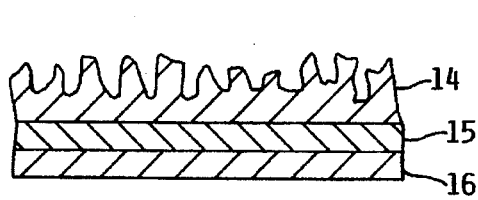
FIG. 2 shows a section view of the laminate structure of the shell of the breast implant of FIG. 1, where the laminate structure has a single thermoplastic elastomer layer.
Figure 3:
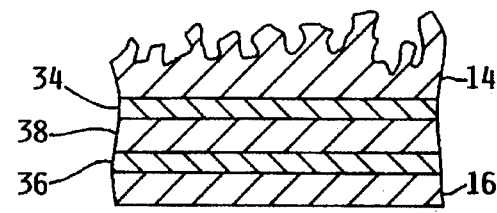
FIG. 3 shows a section view of an alternate embodiment of the laminate structure with two thermoplastic elastomer layers for an invasive structure such as the breast implant of FIG. 1.

The closure 13 is a room temperature vulcanized silicone button seal. The closure 13 is formed of the same laminate of the shell 11 and includes an inner disk shaped silicone layer 20 having a greater diameter than the outer disk shaped layer 22 such that an annular portion 24 of the inner layer 20 extends beyond the outer layer 22. The outer surface of the annular portion 24 is bonded via a vulcanized weld to the inner surface of the shell 11. The outer disk shaped layer 22 has a diameter substantially equal to the diameter of the opening 26 formed by the mandrel in the manufacture of the shell 11. A leaf valve assembly or primary closure 28 is fixed to the inner surface of the disk shaped portion 20. The leaf valve assembly 28 includes an outlet 30 and an inlet disposed adjacent to the center of the disk shaped portion 20. The opposing flap sides of the leaf valve assembly 28 cling together to minimize passage of fluid through the assembly 28. After the closure 13 has been vulcanized to the shell 11 to close the shell 11, a needle filled with the filling material 12 penetrates the closure 13 and extends into the inlet of the leaf assembly 28. The needle is then operated to push the filling material 12 into the shell 11. After the shell has been filled, a pocket of air typically exists in the upper portion of the shell 11. This air may be withdrawn by operation of the needle. The hole formed in the center of the closure 13 by the penetration of the needle is then sealed with a biocompatible silicone to form the domed button seal or secondary closure 32. Depending upon the laminate structure of the shell 11, the water vapor barrier between the layers 20 and 22 includes one thermoplastic elastomer membrane as shown in FIG. 2 or three thermoplastic elastomer membranes as shown in FIG. 3. It should be noted that the closure 13 may alternatively include a valve such as compression valve or septa.

More particularly, the outer and inner layers 14, 16 of the laminate 11 are formed of a biocompatible, generally inert elastomer such as silicone rubber or polyurethane. A silicone rubber or elastomeric shell may include methyl groups on silicon, and further may include trifluoropropyl and phenyl groups on silicon to enhance the barrier function of the silicone elastomer. The silicone elastomer shell may be slick or textured. The silicone rubber which is preferred is dimethylsiloxane.

As stated above, the middle layer 15 is preferably a thermoplastic elastomer. More preferred are thermoplastic elastomers which are block copolymers. Even more preferred are thermoplastic elastomers having styrene block copolymers. Still even more preferred are thermoplastic elastomers having triblock copolymers with styrene endblocks and a midblock of an elastomer polymer selected from olefinic, vinyl, and dienyl based polymers.

The thermoplastic elastomer of the present invention may apply to any block copolymer with the structure A-B-A or $(A-B)_n$ where "A" can be any structure normally regarded as a hard thermoplastic such as polystyrene, poly(methyl methacrylate), polypropylene, poly(a-methylstyrene), polysulfone, poly(silphenylene siloxane), polyurethane, polyethylene, polyester, polyarylester, polycarbonate, polyarylcarbonate, and polyarylether, and "B" can be any polymer normally regarded as elastomeric such as polyisoprene, polybutadiene, polyisobutylene, polydimethylsiloxane, poly(ethylene-co-butylene), polydimethylsiloxane, polyesterurethane, polyetherurethane and where such structure is highly impermeable to water vapor, such as having an $H_2O$ permeability coefficient of 2,290 or less.

The specific ABA thermoplastic elastomers which are preferred are styrene block copolymers with polystyrene endblocks, and polyisoprene, polybutadiene, polyisobutylene, and poly(ethylene-co-butylene) elastomeric midblocks. Other ABA thermoplastic elastomers which may be used have polystyrene as the endblocks and polydimethylsiloxane as the midblock, poly(a-methylstyrene) as the endblocks and polyisoprene and polybutadiene as the midblocks, polyethylene as the endblocks and poly(ethylene-co-butylene) as the midblock, and poly(a-methylstyrene) as the endblocks and polydimethylsiloxane as the midblock.

Preferred $(A-B)_n$ type block copolymers include poly(a-methylstyrene) as the hard segment and polydimethylsiloxane as the soft segment, poly(silphenylene siloxane) as the hard segment and polydimethylsiloxane as the soft segment, polyurethane as the hard segment and polyester or polyether as the soft segment, polyester as the hard segment and polyether as the soft segment, polycarbonate as the hard segment and polydimethylsiloxane as the soft segment, and polycarbonate as the hard segment and polyether as the soft segment. "n" is between 3 and 100.

Of the diblock, triblock, multiblock or star (radial) block copolymers, those having the structure A-B-A or $(A-B)_n$ are preferred. In these preferred structures, the hard thermoplastic endblocks form separate spherical regions or domains which are dispersed in a continuous elastomer phase. At room temperature, these polystyrene domains are hard and act as physical cross-links, tying the elastomer chains together in a three-dimensional network. The domains lose their strength when the material is heated or dissolved in solvents. This then permits the thermoplastic or its solution to flow. When the thermoplastic is cooled or the solvent is evaporated, the domains harden and the thermoplastic regains it integrity or solid elastomeric state.

It should be noted that the hard segment A may differ in the same block. For example, styrene and propylene may be the hard segments and ethylene may the soft rubber segment. Further, one type of block copolymer may be mixed with another type. For example, triblock copolymers may be mixed with diblock copolymers.

It should be noted that block copolymers with structures such as A-B or B-A-B are not included in the present invention as such are not thermoplastic elastomers, since for a continuous network to exist both ends of the elastomer segment must be immobilized in hard domains. These structures are weaker materials resembling conventional unvulcanized synthetic rubbers.

Thermoplastic elastomers that may not be considered as block copolymers but which form part of the present invention include thermoplastic olefins, thermoplastic vulcanizates, thermoplastic urethane, copolyester and copolyamide where such thermoplastic elastomers have hydrophobic properties with preferably an $H_2O$ permeability coefficient of 2,290 or less. Copolyester and copolyamide are thermoplastics in that they combine the processability of thermoplastics with the performance properties of thermoset rubber. Of these, thermoplastic olefins and thermoplastic vulcanizates are preferred with thermoplastic olefins being most preferred.

Thermoplastic olefins may be described as a class of compounds containing polyolefin islands (e.g. polypropylene) in a rubber (e.g. ethylene-propylene-diene monomer based) matrix. Preferred thermoplastic olefins include blends of polypropylene with ethylene-propylene rubbers (EPR) or ethylene-propylene-diene monomer (EPDM) which may be grafted or cross-linked. These thermoplastic elastomers may be referred to as polypropylene/ ethylene-propylene copolymer blends or an ethylene-propylene based thermoplastic elastomer. These thermoplastic elastomers are typically finely interdispersed multiphase systems. Another thermoplastic olefin is propylene-hexene-1 copolymer blend.

Olefinic thermoplastic vulcanizates are rubbers (fully or partially crosslinked) dispersed in an olefinic (usually polypropylene) matrix. These may be described also as rubber islands in a plastic matrix. One olefinic thermoplastic vulcanizate is the Monsanto Santoprene polypropylene/ ethylene-propylene diene monomer. These vulcanizates may also have an isoprene base.

Of the block copolymers, the elastomeric segment or block may be saturated or unsaturated. Polybutadiene and polyisoprene both have one double bond per monomer unit. Poly(ethylene-co-butylene) is completely saturated. Such elastomeric segments are also nonpolar, especially poly (ethylene-co-butylene). Saturated elastomeric segments are preferred.

The hydrocarbon backbones of the elastomeric segments polybutadiene, polyisoprene, poly(ethylene-co-butylene) are important because such impart a hydrophobic nature to the thermoplastic elastomer. With these elastomeric segments, the moisture permeability coefficient for styrene block copolymers is approximately 800 whereas the moisture permeability coefficient for the conventional dimethyl- silicone breast prosthesis shell is approximately 43,000 (units=$10^{10}$×cc (at STP)×cm/sq×cm×sec×cm Hg). In other terms, the styrene block copolymers are approximately 100 times less permeable to water vapor. Olefinic, vinyl, and dienyl elastomeric segments are preferred.

The thermoplastic elastomers may be used as single components or as mixtures with other components such as other thermoplastics. The components may be added to increase the elastomeric properties of the mixture or to enhance the adhesion to the silicone layers.

The thermoplastic elastomers of the present invention may exhibit a broad range of composition. For example, one thermoplastic elastomer may have a low styrene content. Another may have a high molecular weight elastomeric material. Other thermoplastic elastomers may exhibit intermediate properties. Further, if desired, these materials may be mixed. The examples which follow exhibit water vapor barrier properties for use in a laminate structure such as a silicone breast prosthesis envelope.

A further enhancement may be obtained by using hydrochlorocarbon (polyvinylchloride, vinylidene chloride, polychloroprene) based polymers or composite structures containing "islands" of polyolefins (polyethylene, polypropylene, etc.) and/or such hydrochlorocarbons in a matrix of thermoplastic elastomers. These materials exhibit excellent water vapor barrier properties and can be formulated to have a variety of physical properties.

The thermoplastic elastomer membrane 15 may include fillers, resins, tackifying agents, plasticizers, extending agents, antistats as well as one or more thermoplastic elastomers. Fillers include fumed silica, inorganic silicates, calcium carbonate, inert metal oxides such as titanium dioxide, and radio-opaque materials such as barium sulfate.

Resins for adhesion and for matching the extension properties of silicone rubber preferably include rubber phase associating resins. Preferred rubber phase associating resins include hydrocarbon based resins. Preferred hydrocarbon based resins include low-molecular weight hydrocarbon resins. Preferred low-molecular weight hydrocarbon resins include those resins such as Regalrez® 085 (a hydrogenated hydrocarbon resin) and Regalrez® 1094 (a fully hydrogenated styrene-type polymer resin), both of which are manufactured by Hercules Incorporated of Wilmington, Del. Other preferred rubber phase associating resins include wood rosin esters, terpene based resins, urea/melamine, and formaldehyde based resins. Low molecular weight hydrocarbon resins are most preferred. Polystyrene phase associating resins preferably include coumarone-indene resins.

Tackifying agents preferably include those resins which associate primarily with the elastomeric phase and exhibit chemical functionality such as Arcon E-100 which is a deeply hydrogenated hydrocarbon tackifying resin available from Arakawa Chemical U.S.A. Examples include wood-rosin esters and hydrocarbon/terpene resins. The tackifying agent may be dependent on the nature of the substrate (i.e. the polyurethane or silicone layers of the laminate structure.)

Plasticizers include preferably rubber phase associating plasticizers. Preferred rubber phase associating plasticizers include mineral oil plasticizers. Preferred mineral oil plasticizers include paraffinic/napthenic base plasticizers such as Kaydol® mineral oil which is manufactured by Witco of Houston, Tex., polyterpene base plasticizers such as Piccolyte S10 which is manufactured by Hercules Incorporated of Wilmington, Del., mixed olefin base plasticizers such as Wingtack 10 which is manufactured by Goodyear Tire & Rubber of Akron, Ohio, and oil based plasticizers such as Shellflex® 371 which is manufactured by Shell Oil Company of Houston, Tex. Other plasticizers such as waxes and higher boiling hydrocarbon fractions may also be used.

Antistats include amines, glycerol esters, quaternary ammonium compounds, and anionic materials.

As part of the thermoplastic elastomer membrane 15, the thermoplastic elastomer or the combination of thermoplastic elastomers preferably is included in the range of 100% to about 6% by weight, more preferably about 6% to about 30% by weight, and most preferably in the range of about 6% to about 20% by weight. Resins may be excluded from the thermoplastic elastomer membrane 15 or included in an amount of up to about 60% by weight, or more preferably may be included in the amount of between about 20% to about 60%, most preferably between about 40% to about 60% by weight. Plasticizers may be excluded from the thermoplastic elastomer membrane or included in an amount of up to about 50% by weight, more preferably may be included in the amount of between about 20% to about 50%, and most preferably between about 30% to about 40% by weight. Hydrochlorocarbons may be excluded or included in an amount from about 6% to about 30% by weight.

One preferred mixture of thermoplastic elastomers includes a styrene based thermoplastic elastomer and an ethylene-propylene based thermoplastic elastomer. In such a mixture, it should be noted that the styrene-based thermoplastic elastomer is included in a range preferably from about 1% to about 10%, more preferably from about 1% to about 6%, and most preferably from about 2% to about 5% and that the ethylene-propylene based thermoplastic elastomer is included in a range preferably from about 5% to about 99%, more preferably from about 5% to about 30%, and most preferably from about 10% to about 20%.

The process of making the breast prosthesis shell preferably includes dip casting (solvent casting). Each of the silicone layers 14 and 16 is prepared from a dimethylsiloxane solution of a two part silicone elastomer (available from Applied Silicone Corporation of Ventura, Calif., part no. 40,000 which includes the elastomer and cross-linking agent) in xylenes (26% solids w/w). A mandrel in the desired shape is first dipped into the dimethylsiloxane solution, withdrawn from the solution, and the resulting inner dimethylsiloxane layer 16 formed on the mandrel is permitted to set at a temperature of 130° F. (54.44° C.) for about 15 minutes. Then the mandrel with the inner elastomer layer 16 formed thereon is dipped into a thermoplastic elastomer solution. This solution may have a combination of thermoplastic elastomers, as well as resins, plasticizers, etc. The total concentration of the components in the solution may range from about 5% to about 60% (w/w). The mandrel is withdrawn and this membrane barrier 15 is permitted to set at 130° F. (54.44° C.) for about 15 minutes, whereupon the mandrel is dipped again in the dimethylsiloxane solution, withdrawn, and permitted to set at 130° F. (54.44° C.) for 15 minutes to form the outer layer 14. If desired, the mandrel may be yet again dipped in the dimethylsiloxane solution, withdrawn, and permitted to set at 130° F. (54.44° C.). Then the mandrel having the silicone-thermoplastic elastomer-silicone laminate formed thereon is heated at 270° F. (132.22° C.) for about 90 minutes to vulcanize the silicone layers. Prior to or after vulcanization of the silicone layer, the outer silicone layer may be ablated with sodium chloride to form a textured surface on the outer silicone layer, as is shown in FIGS. 2 and 3. After vulcanization of the silicone layer, the shell is permitted to cool to room temperature, and the shell is removed from the mandrel. Such a removal stretches the shell such that the shell or portions of the shell are elongated up to about 800% without the layers being delaminated or any of the layers tearing or breaking.

Formation of the shell is not limited to the preferred solvent or dip casting, but may include spray coating, injection molding, compression molding, or blow molding. Blow, compression, or injection molding may be preferable for thermoplastic olefins, especially thermoplastic olefin vulcanizates.

The thickness of the inner dimethylsiloxane layer 16 of FIGS. 2 and 3 is preferably between about 1 mils (0.00254 cm) to about 18 mils (0.04572 cm), more preferably between about 2 mils (0.00508 cm) to about 18 mils (0.4572 cm), and most preferably between about 7 mils (0.01778 cm) to about 10 mils (0.0254 cm).

The thickness of the thermoplastic elastomer layer 15 of FIG. 2 and of each of the thermoplastic layers of FIG. 3 is preferably between about 2 mils (0.00508 cm) to about 12 mils (0.03048 cm), and more preferably about 2 mils (0.00508 cm) to about 5 mils (0.0127 cm). A thinner thermoplastic elastomer layer tends to promote better adhesion and greater mechanical stability for the three layer laminate structure, but may permit greater fluid flow. Conversely, a thicker thermoplastic elastomer layer may permit less fluid flow, but may provide less adhesive properties for the laminate structure.

The thickness of the outer dimethylsiloxane layer 14 of FIGS. 2 and 3 is preferably between about 1 mils (0.00254 cm) to about 25 mils (0.0635 cm), more preferably between about 2 mils (0.00508 cm) to about 18 mils (0.04572 cm), and most preferably between about 7 mils (0.01778 cm) to about 10 mils (0.0254 cm).

The following examples refer to a number of Kraton® block copolymers available from Shell Oil Company of Houston, Tex. for use in the present invention. The Kraton® G-1650 thermoplastic rubber is a styrene-ethylene/butylene-styrene block copolymer (100%) with a styrene to rubber ratio of 29/71. The Kraton® G-1651 thermoplastic rubber is a styrene-ethylene/butylene-styrene block copolymer (100%) with a styrene to rubber ratio of 33/67. The Kraton® G-1726X thermoplastic rubber includes 30% w/w of the triblock styrene-ethylene/butylene-styrene copolymer and 70% w/w of the diblock styrene-ethylene/butylene copolymer. Kraton® 1726X has a styrene to rubber ratio of 30/70. The Kraton® G-1750X is an ethylene-propylene multi-arm (branched) copolymer of the structure $(AB)_n$ where "A" is ethylene and "B" is propylene. Kraton® G-1750X is derived from an isoprene base and hence is not a thermoplastic olefin.

It should be noted that it is generally preferred that the molecular weights of the thermoplastic elastomers of the present invention, including polymers, copolymers, block, and multi-arm copolymers, fall in the range of about 20,000 to about 300,000, more preferably in the range of about 25,000 to about 250,000, and most preferably in the range of about 30,000 to about 200,000. The resins and plasticizers typically have low molecular weights of about below 1000.

The following Examples 1–26 describe solutions for the hydrophobic thermoplastic elastomer membrane of the laminate according to the present invention where the silicone layers consisted of dimethylsiloxane and where the laminate was formed by the dip casting method described above. It should be noted that the laminates so formed were transparent. The weight percentages are based on the total amount of components excluding the xylene solvent. To make the solutions, the amount of xylene solvent used is from about 1000 to about 4000 grams, typically about 2400 grams.

EXAMPLE 1

Kaydol® Mineral Oil (59.4% w/w), and a mixture of thermoplastic elastomers, Kraton® G-1651 (4.9% w/w) and Kraton® G-1750X (35.7% w/w) were mixed by dissolving the thermoplastic elastomers in xylenes then adding the Kaydol® Mineral Oil to the dispersion with thorough mixing over two or three days at room temperature until dissolution. The total concentration of the components in the xylene solvent was about 50% (w/w).

EXAMPLE 2

Kraton® G-1650 was mixed with xylenes at room temperature over two or three days until dissolution to provide a solution of the pure thermoplastic elastomer at a concentration of 20.8% (w/w).

EXAMPLE 3

Kraton® G-1651 was mixed with xylenes at room temperature over two or three days until dissolution to provide a solution of the pure thermoplastic elastomer at a concentration of 12.5% (w/w).

EXAMPLE 4

Kraton® G-1726X was mixed with xylenes at room temperature over two or three days until dissolution to provide a solution of the pure thermoplastic elastomer at a concentration of 28.6% (w/w).

EXAMPLE 5

Kraton® G-1750X was mixed with xylenes at room temperature over two or three days until dissolution to provide a solution of the pure thermoplastic elastomer at a concentration of 20% (w/w).

EXAMPLE 6(a)

Arcon E-100 (28.4% w/w), Regalrez® 1094 (19.6% w/w), Kaydol® Mineral Oil (30.4% w/w), and a mixture of thermoplastic elastomers, Kraton® G-1651 (2.6% w/w) and Kraton® G-1750X (19.0% w/w) were mixed by dissolving the thermoplastic elastomers in xylenes then adding the other components to the dispersion with thorough mixing at 158° F. (70° C.) for four hours. The total concentration of the components in the xylene solvent was about 50% (w/w).

EXAMPLE 6(b)

Arcon E-100 (31.3% w/w), Regalrez® 1094 (21.9% w/w), Kaydol® Mineral Oil (33.7% w/w), and a mixture of thermoplastic elastomers, Kraton® G-1651 (2.5% w/w) and Kraton® G-1750X (10.6% w/w) were mixed by dissolving the thermoplastic elastomers in xylenes then adding the other components to the dispersion with thorough mixing at 158° F. (70° C.) for four hours. The total concentration of the components in the xylene solvent was 50.0% (w/w).

EXAMPLE 6(c)

Arcon E-100 (37.6% w/w), Regalrez® 1094 (26.3% w/w), Kaydol® Mineral Oil (20.3% w/w), and a mixture of thermoplastic elastomers, Kraton® G-1651 (3.0% w/w) and Kraton® G-1750X (12.7% w/w) were mixed by dissolving the thermoplastic elastomers in xylenes then adding the other components to the dispersion with thorough mixing at 158° F. (70° C.) for four hours. The total concentration of the components in the solution was 45.8% (w/w).

EXAMPLE 6(d)

Arcon E-100 (23.1% w/w), Regalrez® 1094 (32.4% w/w), Kaydol® Mineral Oil (25.0% w/w), and a mixture of thermoplastic elastomers, Kraton® G-1651 (3.7% w/w) and Kraton® G-1750X (15.7% w/w) were mixed by dissolving the thermoplastic elastomers in xylenes then adding the other components to the dispersion with thorough mixing at 158° F. (70° C.) for four hours. The total concentration of the components in the xylene solvent was 40.3% (w/w).

EXAMPLE 7(a)

Arcon E-100 (29.9% w/w), Regalrez® 1085 (19.5% w/w), Kaydol® Mineral Oil (30.1% w/w), and a mixture of thermoplastic elastomers, Kraton® G-1651 (2.6% w/w) and Kraton® G-1750X (18.9% w/w) were mixed by dissolving the thermoplastic elastomers in xylenes then adding the other components to the dispersion with thorough mixing at 158° F. (70° C.) for four hours. The total concentration of the components in the xylene solvent was about 50% (w/w).

EXAMPLE 7(b)

Arcon E-100 (31.3% w/w), Regalrez® 1085 (21.9% w/w), Kaydol® Mineral Oil (33.6% w/w), and a mixture of thermoplastic elastomers, Kraton® G-1651 (2.5% w/w) and Kraton® G-1750X (10.6% w/w) were mixed by dissolving the thermoplastic elastomers in xylenes then adding the other components to the dispersion with thorough mixing at 158° F. (70° C.) for four hours. The total concentration of the components in the xylene solvent was 50.0% (w/w).

EXAMPLE 7(c)

Arcon E-100 (37.6% w/w), Regalrez® 1085 (26.4% w/w), Kaydol® Mineral Oil (20.3% w/w), and a mixture of thermoplastic elastomers, Kraton® G-1651 (3.0% w/w) and Kraton® G-1750X (12.8% w/w) were mixed by dissolving the thermoplastic elastomers in xylenes then adding the other components to the dispersion with thorough mixing at 158° F. (70° C.) for four hours. The total concentration of the components in the xylene solvent was 45.5% (w/w).

EXAMPLE 8

Kraton® G-1651 (12.5% w/w) was mixed with Kaydol® Mineral Oil (35% w/w), Arcon E-100 (30.0% w/w), and Regalrez® 1018 (22% w/w), and the antioxidant stabilizer (available from Ciba-Geigy) Irganox 1010 (0.5% w/w) was added to the solid mixture. This solid mixture was dissolved in xylenes to form a 20% w/w solution by slowly adding to the mixture xylenes at room temperature over a period of two or three days.

EXAMPLE 9

Kraton® G-1651 (12.5% w/w) was mixed with Pennzoil Mineral Oil (35% w/w) (available from Pennzoil Products Company of Houston, Tex.), Arcon E-100 (30.0% w/w) and Regalrez® 1018 (22% w/w), and the stabilizer Irganox 1010 (0.5% w/w) was added to the solid mixture. This solid mixture was dissolved in xylenes to form a 20% w/w solution by slowly adding to the mixture xylenes at room temperature over a period of two or three days.

In the following Examples Nos. 10-24, a solid mixture of Arcon E-100, Regalrez® 1094, Kaydol® Mineral Oil, and a mixture of thermoplastic elastomers, Kraton® G-1651 and Kraton® G-1750X, were slowly added to xylenes at room temperature over a period of two or three days to form a 20% (w/w) solution. Examples 10-24, as well as Examples 1-9 and 25-26, form optimal water vapor barriers for the laminate structure of the present invention.

TABLE 1

| Ex. No. | Kraton® G-1651 (% w/w) | Kraton® G-1750X (% w/w) | Regelr® 1094 (% w/w) | Arcon E-100 (% w/w) | Kaydol® M. Oil (% w/w) |
|---|---|---|---|---|---|
| 10 | 2.5 | 10.6 | 21.9 | 31.3 | 33.7 |
| 11 | 4.5 | 16.8 | 17.5 | 50.1 | 11.2 |
| 12 | 3.8 | 14.3 | 29.7 | 42.7 | 9.5 |
| 13 | 4.0 | 15.0 | 15.6 | 44.8 | 20.5 |
| 14 | 4.5 | 16.8 | 17.4 | 50.0 | 11.3 |
| 15 | 3.8 | 14.3 | 29.7 | 42.7 | 9.5 |
| 16 | 3.5 | 13.0 | 27.0 | 38.8 | 17.7 |
| 17 | 4.0 | 15.0 | 15.6 | 44.8 | 20.5 |
| 18 | 3.0 | 12.7 | 26.3 | 37.6 | 20.3 |
| 19 | 3.0 | 12.6 | 26.0 | 18.5 | 39.9 |
| 20 | 3.7 | 15.7 | 32.5 | 23.2 | 25.0 |
| 21 | 3.7 | 15.4 | 31.9 | 0.0 | 49.0 |
| 22 | 2.5 | 10.6 | 21.9 | 31.3 | 33.7 |
| 23 | 2.5 | 10.6 | 22.0 | 31.3 | 33.7 |
| 24 | 4.4 | 18.8 | 19.4 | 27.7 | 29.8 |

EXAMPLE 25

The methods of Examples 5 and 8 were repeated. As shown in FIG. 3, the two thermoplastic elastomer layers and 36 were formed with the thermoplastic elastomer formulation of Example 8. The thermoplastic elastomer middle layer 38 was formed with the relatively pure thermoplastic elastomer solution of Example 5. Silicone layers 14 and 16 are also included in this embodiment of the laminate structure. Each of the thermoplastic elastomer and silicone layers was formed sequentially on a mandrel by dipping the mandrel in the respective silicone or thermoplastic elastomer formulation or solution and then permitting such layer to set at a temperature of 130° F. (54.44° C.) for about 15 minutes. After the five layers have been so formed, the laminate is heated at 270° F. (132.22° C.) for about 90 minutes to vulcanize the silicone layers. Then the laminate is permitted to cool to room temperature, and the shell is removed from the mandrel. Such a removal stretches the shell such that the shell or portions of the shell are elongated up to about 800% without the layers being delaminated or any of the layers tearing or breaking.

EXAMPLE 26

The methods of Examples 5 and 9 were repeated. As shown in FIG. 3, the two thermoplastic elastomer layers 34 and 36 were formed with the thermoplastic elastomer formulation of Example 9. The thermoplastic elastomer middle layer 38 was formed with the relatively pure thermoplastic elastomer solution of Example 5. Silicone layers 14 and 16 are also included in this embodiment of the laminate structure. Each of the thermoplastic elastomer and silicone layers was formed sequentially on a mandrel by dipping the mandrel in the respective silicone or thermoplastic elastomer formulation or solution and then permitting such layer to set at a temperature of 130° F. (54.44° C.) for about 15 minutes. After the five layers have been so formed, the laminate is heated at 270° (132.22° C.) for about 90 minutes to vulcanize the silicone layers. Then the laminate is permitted to cool to room temperature, and the shell is removed from the mandrel. Such a removal stretches the shell such that the shell or portions of the shell are elongated up to about 800% without the layers being delaminated or any of the layers tearing or breaking.

In each of the examples 25 and 26, the thickness of the middle layer 38 is preferably about 6 mils to about 8 mils (0.01524 cm to 0.02032 cm) and the thickness of each of the layers 34 and 36 is preferably about 2 mils (0.00508 cm). The thickness of the silicone layers 14 and 16 are those as described above with respect to the laminate structure of FIG. 2.

The purposes of the three thermoplastic elastomer layers of FIG. 3 are to even further minimize moisture permeation through the laminate structure and to add a mechanical layer of protection in case of a tear in one of the thermoplastic elastomer or silicone layers.

It should be noted that, if desired, the middle layer 38 may be a silicone rubber or polyurethane.

Figure 4:
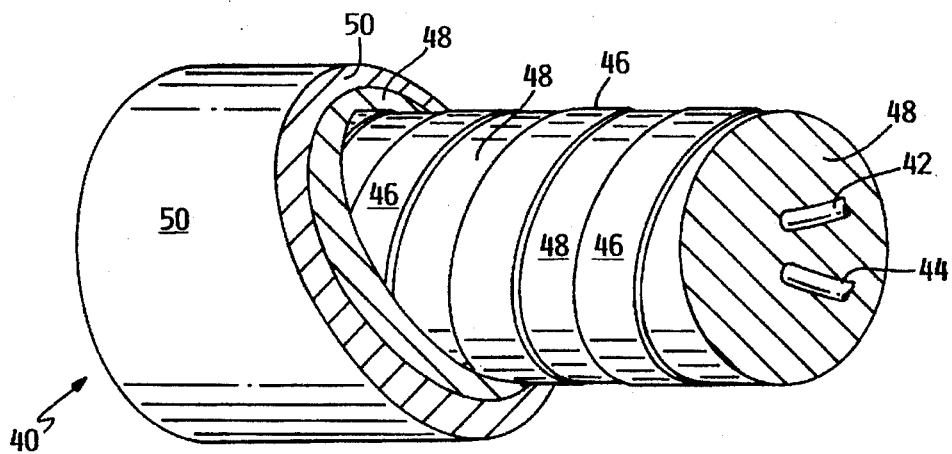
FIG. 4 shows a partially cut-way perspective view of a catheter coated with a laminate structure of the present invention.

As shown in FIG. 4, a catheter 40 includes a pair of electrical leads 42, 44, and a spiral coil 46. The leads 42, 44 may be formed of a wide variety of relatively inexpensive metals in light of the water vapor barrier or coating 48 formed about the leads 42, 44 and spiral coil 46. A biocompatible layer 50 is laminated to the coating 48. The water vapor barrier 48 may be formed of any of the thermoplastic elastomers or thermoplastic elastomer formulations of the present invention. The layer 50 may be formed of any of the biocompatible materials described for use in the outer layer 14 of the shell 11, including silicone and polyurethane.

The reference numerals 42, 44 represent metal leads or any other catheter element which may be subject to corrosion or adversely affected by moisture and which permit an operation at the distal end of the catheter, control at the proximal end of the catheter, and communication therebetween. The reference numerals 46 represent a spiral coil or any other element providing rigidity and flexibility to the catheter and which may be subject to corrosion or adversely affected by moisture. The thermoplastic elastomer membrane 48 of the present invention permits a wide variety of materials to be used for the elements 42, 44, and 46. Such materials may include metals, such as stainless steel, which are less expensive than gold conventionally used in catheters because it is relatively corrosion resistant.

Figure 5:
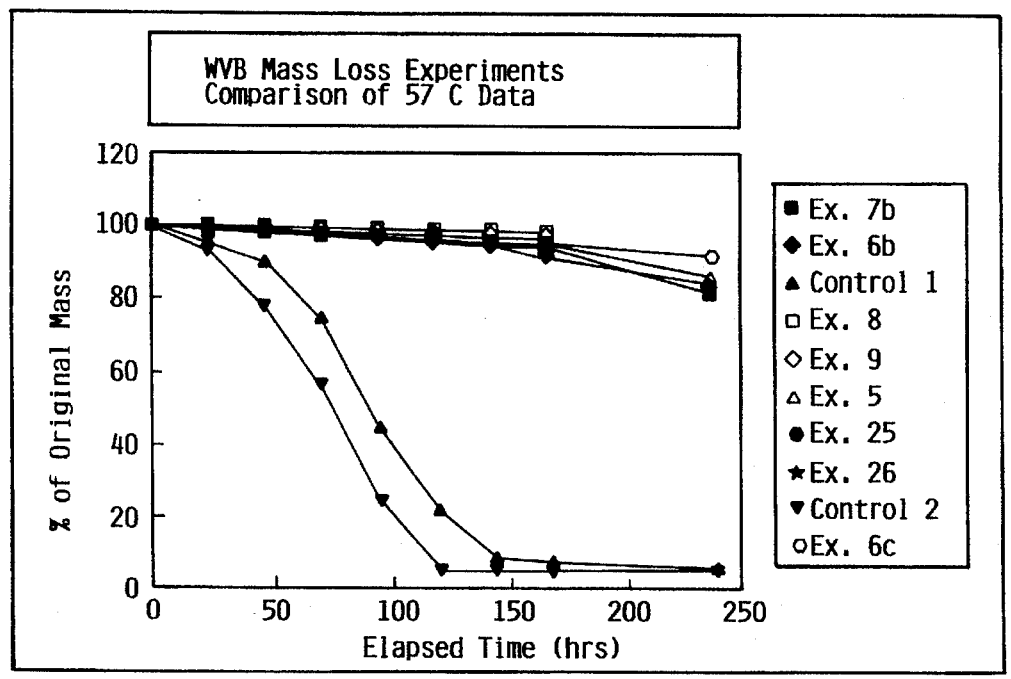
FIG. 5 is a chart depicting the water barrier effects of several laminate structures consisting of silicone rubber with an inner layer of a thermoplastic elastomer fluid barrier.

The water vapor barrier mass loss experiment charted in FIG. 5 used breast prostheses as shown in FIG. 1 filled with 160–200 cc of deionized chemically pure $H_2O$. The prostheses were placed on racks in an oven at 134.6° F. (57° C.) and weighed daily. Examples 5, 7(b), 9, 25, and 26 were tested over a period of 240 hours (10 days, but not weighed on days 8 and 9), and Examples 6(b), 6(c), and 8 were tested over a period of 168 hours (seven days). The control examples included prostheses having conventional silicone rubber shells. The "y" axis represents the mass of the deionized water plus the mass of the prosthesis. The control shells lost substantially all water within seven days; the mass value of each of the controls on the eighth, ninth and tenth days reflects the mass of the silicone rubber shells.

Figure 6:
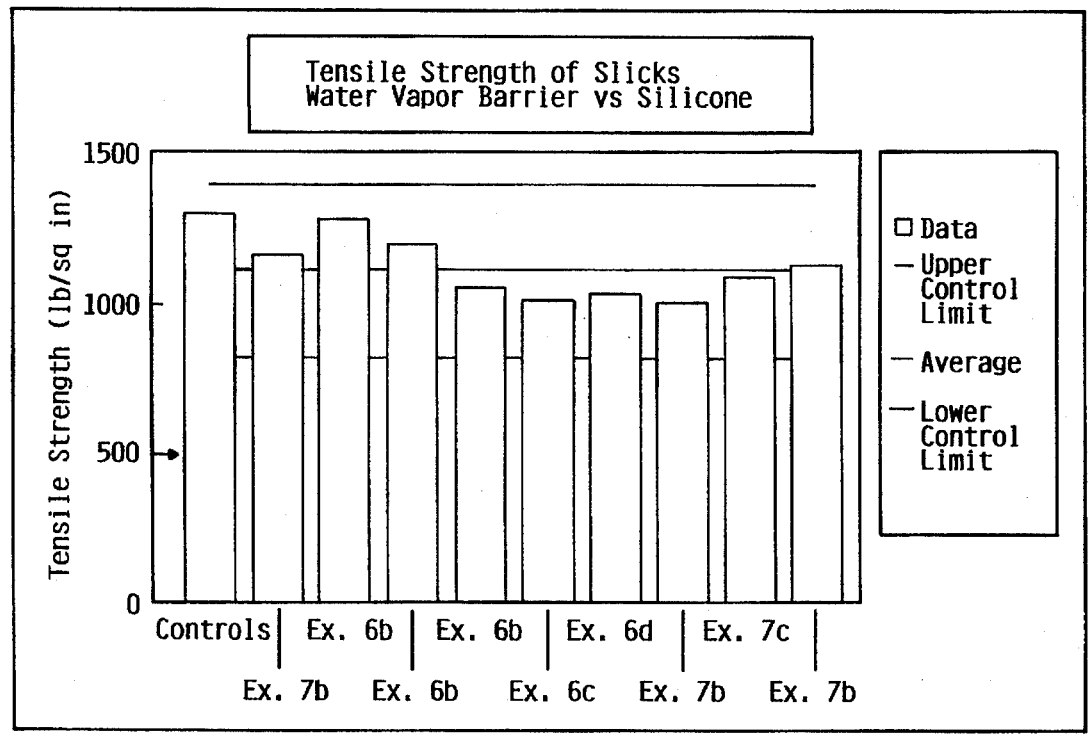
FIG. 6 is a chart depicting comparable physical (tensile) strength for water vapor barrier laminate breast prosthesis shells as compared to silicone rubber shells.
Figure 7:
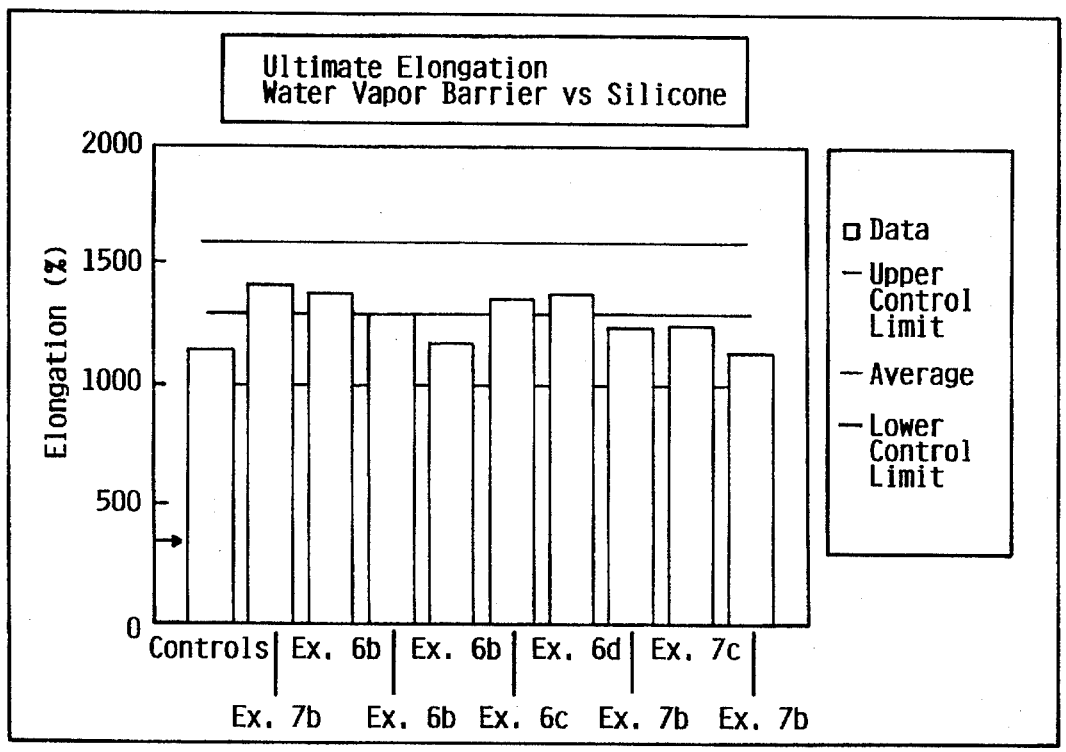
FIG. 7 is a chart depicting the elongation properties of water vapor barrier laminate breast prosthesis shells as compared to silicone rubber shells.
Figure 8:
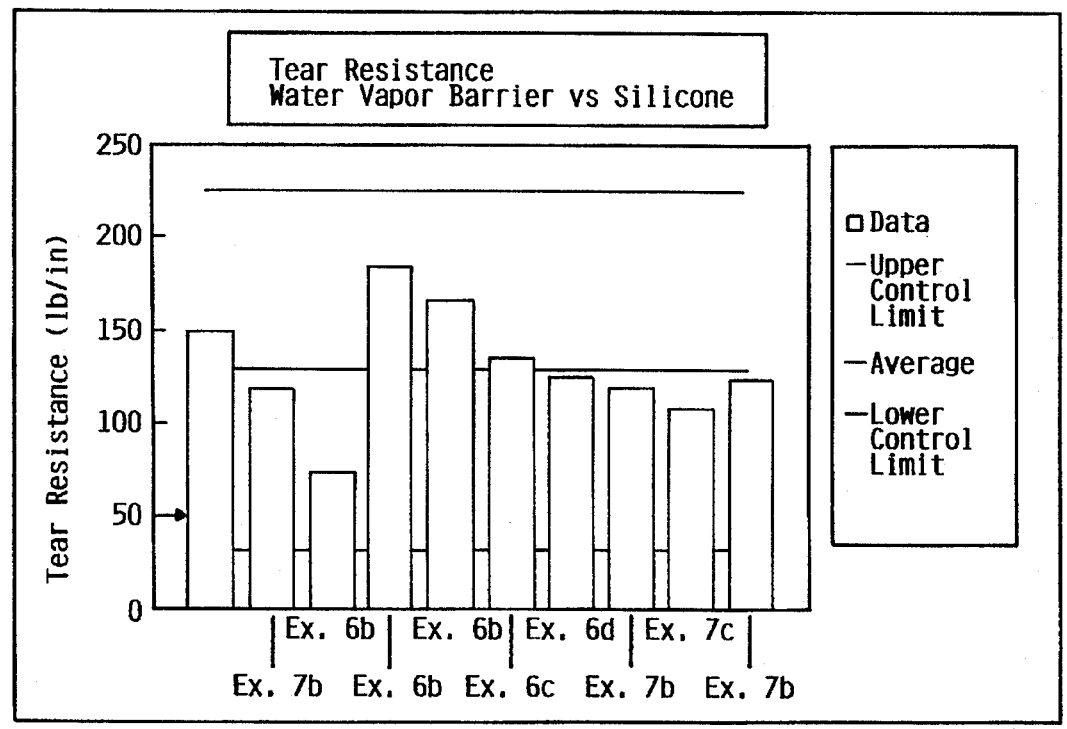
FIG. 8 is a chart depicting the tear resistance of water vapor barrier breast prostheses as compared to silicone rubber shells.

The tensile strength and ultimate elongation data charted in FIGS. 6 and 7 were determined by the ASTM method D-412. The tear resistance data charted in FIG. 8 was determined by the ASTM method 624. The values shown by the bars in FIGS. 6–8 are reproduced below in Table 2.

TABLE 2

| Ex. No. | FIG. 4 (Tns. Strg.) | FIG. 5 (Elongatn.) | FIG. 6 (Tear Res.) |
|---|---|---|---|
| Cntrl | 1305 | 1150 | 150 |
| 7b | 1161 | 1412 | 118 |
| 6b | 1282 | 1380 | 73 |
| 6b | 1195 | 1290 | 184 |
| 6b | 1045 | 1170 | 166 |

TABLE 2-continued

| Ex. No. | FIG. 4 (Tns. Strg.) | FIG. 5 (Elongatn.) | FIG. 6 (Tear Res.) |
|---|---|---|---|
| 6c | 1007 | 1350 | 135 |
| 6d | 1024 | 1370 | 125 |
| 7b | 992 | 1240 | 119 |
| 7c | 1081 | 1250 | 108 |
| 7b | 1116 | 1130 | 123 |

The ASTMF703 specifications for the respective tensile strength, elongation, and tear resistance tests are 500 pounds per square inch (35.2 kilograms per square centimeter), 350%, and 50 pounds per inch (8.95 kilograms per centimeter). These specifications are denoted by the respective arrows in FIGS. 6–8. The upper and lower control limits in FIGS. 6–8 indicate standard error.

For the laminates according to the present invention, it is preferred that the laminates have tensile strength, elongation, and tear resistance values of at least 500 pounds per square inch (35.2 kilograms per square centimeter), 350%, and 50 pounds per inch (8.95 kilograms per centimeter) when determined by the ASTM methods D-412 and 624. It is more preferred that the laminates have tensile strength, elongation, and tear resistance values of at least 750 pounds per square inch 52.8 kilograms per square centimeter), 750%, and 75 pounds per inch (13.4 kilograms per centimeter) when determined by the ASTM methods D-412 and 624. It is most preferred that the laminates have tensile strength, elongation, and tear resistance values of at least 900 pounds per square inch (63.3 kilograms per square centimeter), 1000%, and 100 pounds per inch (17.9 kilograms per centimeter) when determined by the ASTM methods D-412 and 624.

It should be noted that for the purposes of this application the term "rubber" is used interchangeably with the term "elastomer." It should be further noted that laminate structures which are transparent are preferred.

It should further be noted that biocompatible for the purposes of the present invention means that which is inert or generally considered to be inert when inside of the body or when in contact with body tissue or body fluids. Biocompatible materials include silicone rubbers and polyurethane rubbers. Biocompatible silicone rubbers include dimethylsiloxane rubbers and those rubbers having methyl, trifluoropropyl and phenyl groups on silicon.

A hydrophobic laminate structure means a laminate structure having a significant concentration (more than about 6% by weight) of a material (or composite of materials) with an $H_2O$ permeability coefficient of 2,290 or less as measured in accordance with ASTM D 1434-82 and ASTM E 96-80 (Procedure E) at a temperature of 37.8° C. in units of $10^{10} \times cc$ (at STP)×cm/sq cm×sec×cm Hg. Such permeability coefficients for some materials are shown below in Table 3.

TABLE 3

| Material | $H_2O$ permeability coefficient |
|---|---|
| Kraton ® G-1650 | 760 at 37.8° C. |
| Kraton ® G-1651 | 860 at 37.8° C. |
| Polyisoprene | 2,290 at 25° C. |
| Unplasticized polyvinylchloride | 275 at 25° C. |
| polystyrene | 1,200 at 25° C. |

TABLE 3-continued

| Material | H₂O permeability coefficient |
| --- | --- |
| polyethylene (high density) | 12 at 25° C. |
| polyethylene (low density) | 90 at 25° C. |
| polydimethyl siloxane | 43,000 at 35° C. |
| poly (vinylidene chloride) | 0.5 at 25° C. |
| poly (chloroprene) | 9.0 at 25° C. |

The hydrophobic or water vapor barrier structure of the present invention preferably includes a significant concentration of a material or composite of materials (more than about 6% by weight) having such a permeability coefficient at or under that of polyisoprene (2,290), more preferably at or under that of polystyrene (1200), and most preferably at or under that of low density polyethylene (90).

It should be noted that some of the Kraton® D-series of block copolymers may be used for the thermoplastic elastomer layer. These include the styrene-ethylene-propylene block copolymer.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

What is claimed is:

1. A biocompatible hydrophobic laminate structure for enveloping matter, the laminate structure and matter to be introduced into a host's body, the laminate structure comprising:
   a) at least one rubber layer which is biocompatible with an inside portion of the body or body tissue or body fluid;
   b) a hydrophobic, water vapor barrier membrane laminated on each rubber layer to minimize the permeation of moisture through the laminate structure;
   c) with the hydrophobic water vapor barrier membrane being isolated from the inside portion of the body or body tissue or body fluid by the at least one rubber layer; and
   d) with the hydrophobic membrane comprising a thermoplastic elastomer which is substantially impermeable to water vapor and which is present in the membrane in a concentration effective such that the membrane also is substantially impermeable to water vapor and such that, when formed as an implantable water-based fluid enveloping structure, said structure prevents substantial permeation of the water vapor contained therein, barring rupture of said implantable structure.

2. The biocompatible laminate structure of claim 1 wherein the thermoplastic elastomer comprises a block copolymer.

3. The biocompatible laminate structure of claim 2 wherein the block copolymer is selected from the group consisting of block copolymers having the structure A-B-A and (A-B)$_n$ where A is a thermoplastic block and B is an elastomeric block.

4. The biocompatible laminate structure of claim 3 wherein A is polystyrene.

5. The biocompatible laminate structure of claim 3 wherein B is selected from the group consisting of olefinic, vinyl, and dienyl polymers.

6. The biocompatible laminate structure of claim 3 wherein B is selected from the group consisting of polyisoprene, polybutadiene, polyisobutylene, and ethylene/butylene polymers.

7. The biocompatible laminate structure of claim 3 wherein A is polystyrene and B is selected from the group consisting of polyisoprene, polybutadiene, polyisobutylene, and ethylene/butylene polymers.

8. The biocompatible laminate structure of claim 3 wherein A is selected from the group consisting of polystyrene, poly(methyl methacrylate), polypropylene, poly(α-methylstyrene), polysulfone, polyethylene, polyester, polyarylester, and polyarylether and wherein B is selected from the group consisting of polyisoprene, polybutadiene, polyisobutylene, and poly(ethylene-co-butylene).

9. The biocompatible laminate structure of claim 3 wherein B is thermodynamically incompatible with A.

10. The biocompatible laminate structure of claim 1 wherein the thermoplastic elastomer comprises an ethylene-propylene based copolymer.

11. The biocompatible laminate structure of claim 10 wherein the thermoplastic elastomer comprises an ethylene-propylene multi-arm copolymer.

12. The biocompatible laminate structure of claim 1 wherein the thermoplastic elastomer comprises an ethylene-propylene based copolymer and a styrene block copolymer.

13. The biocompatible laminate structure of claim 1 wherein the thermoplastic elastomer includes an H₂O permeability coefficient at about that of polyisoprene or less as measured by ASTM E 96-80 (Procedure E).

14. The biocompatible laminate structure of claim 1 wherein the hydrophobic membrane further comprises a resin and a plasticizer mixed in with the thermoplastic elastomer.

15. The biocompatible laminate structure of claim 1 wherein the hydrophobic membrane further comprises a hydrochlorocarbon based polymer mixed in with the thermoplastic elastomer.

16. The biocompatible laminate structure of claim 15 wherein the hydrochlorocarbon based polymer is selected from the group consisting of vinylidene chloride and polychloroprene.

17. The biocompatible laminate structure of claim 15 wherein the hydrophobic membrane comprises a composite structure of at least one polyolefin and at least one hydrochlorocarbon.

18. The biocompatible laminate structure of claim 1 wherein the thermoplastic elastomer is selected from the group consisting of thermoplastic olefins, thermoplastic vulcanizates, thermoplastic copolyester and thermoplastic copolyamide where such thermoplastic elastomers have hydrophobic, water vapor barrier properties with an H₂O permeability coefficient at about that of polyisoprene or less as measured by ASTM E 96-80 (Procedure E).

19. The biocompatible laminate structure of claim 1 wherein the biocompatible rubber layer is selected from the group consisting of silicone rubbers and polyurethane.

20. The biocompatible laminate structure of claim 19 wherein the biocompatible rubber layer comprises silicone rubber.

21. The biocompatible laminate structure of claim 1 and further comprising another rubber layer, with the hydrophobic membrane being laminated between the rubber layers.

22. The biocompatible laminate structure of claim 21, further comprising at least one more of said hydrophobic membrane and at least one more rubber layer such that one rubber layer is sandwiched between two hydrophobic membranes which in turn are sandwiched between two rubber layers.

23. The laminate structure of claim 1 having a tensile strength of at least 900 pounds per square inch and a tear resistance of at least 100 pounds per inch, and being elongatable up to 1000% without delamination.

24. The laminate structure of claim 1 wherein the laminate structure is transparent.

25. The biocompatible laminate structure of claim 1 wherein the thermoplastic elastomer is less permeable to water vapor than the at least one rubber layer by at least one order of magnitude when measured in accordance with ASTM E 96-80 (Procedure E) in units of $10^{10} \times cc$ (at STP)$\times cm$/sq $cm \times sec \times cm$ Hg.

26. A breast prosthesis shell comprising:
   a) at least one elastomeric layer having outer and inner surfaces, the outer surface of the at least one elastomeric layer being biocompatible with an inside portion of a host's body; and
   b) a hydrophobic, water vapor barrier membrane on the inner surface of each elastomeric layer to minimize the permeation of moisture through the breast prosthesis shell, with the hydrophobic membrane being isolated from the inside portion of the body or body tissue or body fluid by the at least one elastomeric layer, the hydrophobic membrane comprising a thermoplastic elastomer which is substantially impermeable to water vapor such that, when the shell is formed as an implantable water-based fluid enveloping structure, said structure prevents substantial permeation of the water vapor contained therein, barring rupture of said implantable structure.

27. A breast prosthesis shell comprising:
   a) a pair of silicone elastomer layers; and
   b) a hydrophobic, water vapor barrier membrane laminated between the silicone elastomer layers so as to be isolated from body tissue or filling for the shell and comprising a styrene block thermoplastic elastomer or a styrene derivative block thermoplastic elastomer which is substantially impermeable to water vapor such that, when the shell is formed as an implantable water-based fluid enveloping structure, said structure prevents substantial permeation of the water vapor contained therein, barring rupture of said implantable structure.

28. A breast prosthesis comprising: a shell with an outer surface which is compatible with an inside portion of a host's body, a water-based filling material for the shell, closure means on the shell for sealing the water-based filling material in the shell, and a hydrophobic, water vapor barrier membrane laminated on the shell inwardly of the outer surface with the water vapor barrier membrane being isolated from the inside portion of the body or body tissue or body fluid by the shell, and comprising a thermoplastic elastomer which is substantially impermeable to water vapor such that permeation of water vapor through the membrane from the water-based filling material or body is minimized and such that, when the prosthesis is formed as an implantable water-based fluid enveloping structure, said structure prevents substantial permeation of the water vapor contained therein, barring rupture of said implantable structure.

29. A biocompatible hydrophobic laminate structure for enveloping matter, the laminate structure and matter to be introduced into a host's body, the laminate structure comprising:
   a) at least one rubber layer which is biocompatible with the inside of the body or body tissue or body fluid; and
   b) a hydrophobic, water vapor barrier membrane laminated on each rubber layer to minimize the permeation of moisture through the laminate structure, with the hydrophobic membrane being isolated from the inside portion of the body or body tissue or body fluid by the at least one rubber layer, the hydrophobic membrane comprising a thermoplastic elastomer comprised of a block copolymer selected from the group consisting of block copolymers having the structure A-B-A and (A-B)$_n$ where A is a thermoplastic block and B is an elastomeric block, wherein B comprises a hydrocarbon, and wherein the block copolymer is substantially impermeable to water vapor such that, when formed as an implantable water-based fluid enveloping structure, said structure prevents substantial permeation of the water vapor contained therein barring rupture of said implantable structure.

30. A biocompatible hydrophobic laminate structure for enveloping matter, the laminate structure and matter to be introduced into a host's body, the laminate structure comprising:
   a) at least one rubber layer which is biocompatible with an inside of the body or body tissue or body fluid, with the at least one rubber layer comprising a rubber selected from the group consisting of silicone and polyurethane;
   b) a hydrophobic, water vapor barrier membrane laminated on each rubber layer to minimize permeation of moisture through the laminate structure;
   c) with the hydrophobic, water vapor barrier membrane being isolated from the inside portion of the body or body tissue or body fluid by the at least one rubber layer,
   d) with the hydrophobic, water vapor barrier membrane comprising a thermoplastic elastomer; and
   e) with the thermoplastic elastomer being substantially less permeable to water vapor than either the silicone or polyurethane of each rubber layer such that, when formed as an implantable water-based fluid enveloping structure, said structure prevents substantial permeation of the water vapor contained therein, barring rupture of said implantable structure.

31. The biocompatible hydrophobic laminate structure of claim 30 wherein the thermoplastic elastomer is less permeable to water vapor than one of the silicone and polyurethane of each rubber layer by at least one order of magnitude when measured in accordance with ASTM E 96-80 (Procedure E) in units of $10^{10} \times cc$ (at STP)$\times cm$/sq $cm \times see \times cm$ Hg.

32. A biocompatible hydrophobic laminate structure for enveloping matter, the laminate structure and matter to be introduced into a host's body, the laminate structure comprising:
   a) at least one rubber layer which is biocompatible with an inside of the body or body tissue or body fluid, with each rubber layer optionally comprising polyurethane;
   b) a hydrophobic, water vapor barrier membrane laminated on each rubber layer to minimize permeation of moisture through the laminate structure;
   c) with the hydrophobic, water vapor barrier membrane being isolated from the inside portion of the body or body tissue or body fluid by the at least one rubber layer;
   d) with the hydrophobic, water vapor barrier membrane comprising a thermoplastic elastomer; and
   e) with the thermoplastic elastomer being substantially less permeable to water vapor than polyurethane such that, when formed as an implantable water-based fluid enveloping structure, said structure prevents substantial permeation of the water vapor contained therein, barring rupture of said implantable structure.

* * * * *